(12) United States Patent
Nakamura

(10) Patent No.: US 7,578,391 B2
(45) Date of Patent: Aug. 25, 2009

(54) MEDICAL TREATMENT KIT

(75) Inventor: Hiroyuki Nakamura, Fukuoka (JP)

(73) Assignee: Aglis Co., Ltd., Fukuoka (JP)

( * ) Notice: Subject to any disclaimer, the term of this patent is extended or adjusted under 35 U.S.C. 154(b) by 0 days.

(21) Appl. No.: 10/571,993

(22) PCT Filed: Dec. 17, 2004

(86) PCT No.: PCT/JP2004/018911

§ 371 (c)(1),
(2), (4) Date: Mar. 15, 2006

(87) PCT Pub. No.: WO2005/092232

PCT Pub. Date: Oct. 6, 2005

(65) Prior Publication Data

US 2007/0095679 A1    May 3, 2007

(30) Foreign Application Priority Data

Mar. 29, 2004    (JP) .............................. 2004-095061
Sep. 29, 2004    (JP) .............................. 2004-284242

(51) Int. Cl.
*B65D 71/00*    (2006.01)
(52) U.S. Cl. ...................... 206/572; 206/558; 206/223; 206/363; 206/471
(58) Field of Classification Search ................ 206/572, 206/223, 216, 370, 438, 439, 461, 467, 471, 206/363, 558
See application file for complete search history.

(56) References Cited

U.S. PATENT DOCUMENTS

| | | | | |
|---|---|---|---|---|
| 3,954,174 A | * | 5/1976 | Kraus | .......................... 206/572 |
| 4,170,300 A | * | 10/1979 | Pick | .......................... 206/365 |
| 4,989,733 A | | 2/1991 | Patry | |
| 5,163,557 A | | 11/1992 | Sokolowski | |
| 5,766,715 A | * | 6/1998 | Garconnet | .................. 428/40.1 |
| 6,372,313 B1 | | 4/2002 | D'Alessio et al. | |
| 6,622,864 B1 | * | 9/2003 | Debbs et al. | ................. 206/438 |
| 7,017,774 B2 | * | 3/2006 | Haedt | .......................... 220/735 |
| 7,048,120 B2 | * | 5/2006 | Pond | .......................... 206/366 |
| 2004/0004019 A1 | * | 1/2004 | Busch | ......................... 206/571 |

FOREIGN PATENT DOCUMENTS

| | | |
|---|---|---|
| JP | 09-103465 | 4/1997 |
| JP | 10-086977 | 4/1998 |
| JP | 2000-225126 | 8/2000 |
| JP | 2000-271150 | 10/2000 |
| JP | 2002-102252 | 4/2002 |

* cited by examiner

*Primary Examiner*—J. Gregory Pickett
*Assistant Examiner*—Jenine M Pagan
(74) *Attorney, Agent, or Firm*—Sughrue Mion, PLLC

(57) ABSTRACT

To provide a medical kit capable of housing a medical instrument and a medicinal solution together, whose manufacturing is easy. In a medical kit (1) provided with a medical instrument housing portion (2) housing a medical instrument and sealed with a covering material (7), and a medicinal solution housing portion (4) housing a medicinal solution and sealed with a covering material (9), a medical kit (1) is of a constitution consisting of the medical instrument housing portion (2) and the medicinal solution housing portion (4) being detachably fitted, a mounting portion (3) preferably being formed in a flange portion (5) of the medical instrument housing portion (2) where the medicinal solution housing portion (4) can be detachably fitted.

12 Claims, 3 Drawing Sheets

MEDICAL TREATMENT KIT

CROSS-REFERENCE TO RELATED APPLICATIONS

The present application is base on International Application PCT/JP2004/018911 filed on Dec. 17, 2004, and Japanese Patent Applications No. 2004-095061 filed on Mar. 29, 2004, and No. 2004-284242 filed on Sep. 29, 2004 which applications are incorporated herein by reference in its entirety.

TECHNICAL FIELD

The present invention relates to a medical kit housing medical instruments, such as a syringe, gauze, a cotton ball, tweezers, and the like, and a medicinal solution, such as a medicinal solution for disinfection.

BACKGROUND ART

Currently, medical kits are used in dialysis rooms or treatment rooms/operation rooms and the like for use in disinfection of an affected area before and after treatment or for use in a treatment, wherein hygiene products and miscellaneous articles for medical use, such as gauze, tweezers, a cotton-tip applicator, a cotton ball, and adhesive tape, and medical instruments, are assorted in a tray or a bag to form a kit. Since such a medical kit, being disposable, is not only easy to use but also contributes to prevention of hospital acquired infection, cost reduction, including labor costs, labor saving and streamlining of work, and the like, the demand therefor is expected to expand more and more in the future.

Prior art medical kits of this type have been disclosed, for instance, constituted in such a way that a fraction of the housing portion for housing medical instruments, such as a syringe, gauze, a cotton ball, and tweezers, is formed to be foldable, where a medicinal solution for disinfection and the like is to be stored (see Japanese Patent Application Laid-Open No. 2000-225126), constituted in such a way that a removable tray is fitted into at least one compartment area for housing a medical article (see Japanese Patent Application Laid-Open No. 2002-102252), or provided with a medical instrument housing portion for housing a medical instrument and a liquid housing portion to be filled with a liquid for medical use (see Japanese Patent Application Laid-Open No. 2000-271150), and the like.

DISCLOSURE OF THE INVENTION

Problems to be Solved by the Invention

As a matter of fact, when actually using a medical kit for use in disinfection of the affected area before and after treatment or for use in a treatment on a medical scene, a medicinal solution for disinfection becomes always necessary. However, with the medical kit proposed in Japanese Patent Application Laid-Open No. 2000-225126 and the like, although a space is provided for placing a medicinal solution for disinfection (liquid holding portion), the liquid holding portion has to be filled with the medicinal solution for disinfection each time it is to be used, which is inconvenient. Moreover, since many of these types of medical kit are generally designed to be compact with disposal in mind, there is no margin in the width, the length, and the depth, such that filling with a medicinal solution for disinfection has to be performed cautiously, which is even more complicated and inconvenient. In addition, important waste has been pointed out, as there is a tendency to fill the liquid holding portion with an amount of medicinal solution for disinfection that is more than necessary. In particular, such a problem is serious in a large-scale dialysis room treating several patients simultaneously and the like, and a quick resolution is strongly sought.

Thus, one can think that if a suitable amount of medicinal solution for disinfection were pre-housed in the medical kit, it would be very convenient; however, since the kit proposed, for instance, in Japanese Patent Application Laid-Open No. 2000-271150, is constituted in such a way that after a liquid housing portion is filled with a liquid for medical use, medical instruments are housed in the medical instrument housing portion, and sterilization treatment, such as EOG sterilization, electron beam sterilization, gamma beam sterilization, and autoclave sterilization, is performed, there is the possibility of disrupting the housing portion that encapsulates the medicinal solution for disinfection, provoking liquid leakage, bursting depending on circumstances, or deterioration of the medicinal solution for disinfection due to the sterilization treatment.

In consideration of the foregoing problems, the present invention provides a medical kit, which is a medical kit pre-housing a medicinal solution, such as a medicinal solution for disinfection (including antiseptic agent solutions authorized by the Pharmaceutical Affairs Law), together with medical instruments, such as a syringe, gauze, a cotton ball, and tweezers (including those authorized as hygiene products, medical instruments, and miscellaneous articles for medical use), and which can be constituted in such a way that the influence of the sterilization treatment on the medical instruments is not exerted on the medicinal solution.

Means to Solve the Problems

The present invention provides a medical kit provided with a medicinal solution housing portion comprised of a medicinal solution housing container provided with a medicinal solution housing chamber, the medicinal solution housing chamber housing a medicinal solution, and the medicinal solution housing chamber being closed by covering (sealed by covering) with a covering material, a medical instrument housing portion, which is a separate body from the above medicinal solution housing container, comprised of a medical instrument housing container provided with a medical instrument housing chamber, a medical instrument being housed inside the medical instrument housing chamber, and the medical instrument housing chamber being closed by covering with a different covering material from the aforementioned covering material, and provided with a constitution comprised of the medicinal solution housing portion and the medical instrument housing portion engaged for integration.

The medical kit of the present invention can be made into a medical kit in which, on one hand, a medicinal solution is housed in a medicinal solution housing chamber of a medicinal solution housing container, the medicinal solution housing chamber being closed by covering with a covering material; on the other hand, a medical instrument is housed inside the medical instrument housing chamber of a medical instrument housing container, the medical instrument housing chamber being closed by covering with a covering material and treated by sterilization, and the medicinal solution housing container and the medical instrument housing container being engaged for integration.

Effect of the Invention

Since the medical kit of the present invention has such constitution that the medical instrument housing portion (medical instrument housing container) and the medicinal solution housing portion (medicinal solution housing container) are separate bodies, and the medicinal solution housing portion is engaged to be integrated with the medical instrument housing portion, there is no major technical difficulty in relation to the actual manufacturing; the cost of manufacturing equipment is also low, and it can be manufactured easily.

From the user's perspective, since a medicinal solution, such as a medicinal solution for disinfection, is housed in the medical kit, medical manipulations, such as disinfection manipulation and dialysis, can be carried out easily without having to fill the liquid holding portion with the medicinal solution for disinfection each time. In addition, since medicinal solution in an amount that is necessary and sufficient is pre-housed, the medicinal solution is not overused, allowing wasting of the medicinal solution to be avoided, which can contribute to laborsaving and cost reduction. Thus, the user can also enjoy a number of merits from the points of user-friendliness, economics, functionality, and the like.

In addition, if we suppose a constitution in which the medical instrument housing portion and the medicinal solution housing portion are closed by being covered with one covering material, since when the medical instrument housing portion is treated by sterilization, the medicinal solution housing portion simultaneously receives the sterilization treatment, there is the possibility that the medicinal solution deteriorates due to this sterilization treatment, that the medicinal solution housing portion explodes due to evaporation of the medicinal solution, and the like, such that not only tremendous costs in equipment investment is to be expected, but the sterilization treatment method, the material quality of the covering material, and the like also have to be limited.

In contrast to this, since the medical kit of the present invention consists of a constitution in which the medical instruments and the medicinal solution are housed separately and covered separately, the medical instrument housing portion alone can be treated by sterilization, and the medicinal solution housing portion can be engaged and integrated with (fitted in) the medical instrument housing portion after the sterilization treatment, allowing the medicinal solution inside the medicinal solution housing portion not to be affected by the influence of the sterilization treatment on the medical instruments. Therefore, since sterilization treatment methods, such as electron beam sterilization, radiation sterilization, and EOG sterilization, the type and the concentration of the medicinal solution, the material quality of the covering material, and the like can be suitably selected according to the application, the medical kit of the invention is excellent on the points of user-friendliness, functionality, safety, manufacturing cost and the like.

BEST MODE FOR CARRYING OUT THE INVENTION

In the following, examples of the present invention will be described using figures. However, the scope of the present invention is not limited to the examples described in the following.

Figure 1:
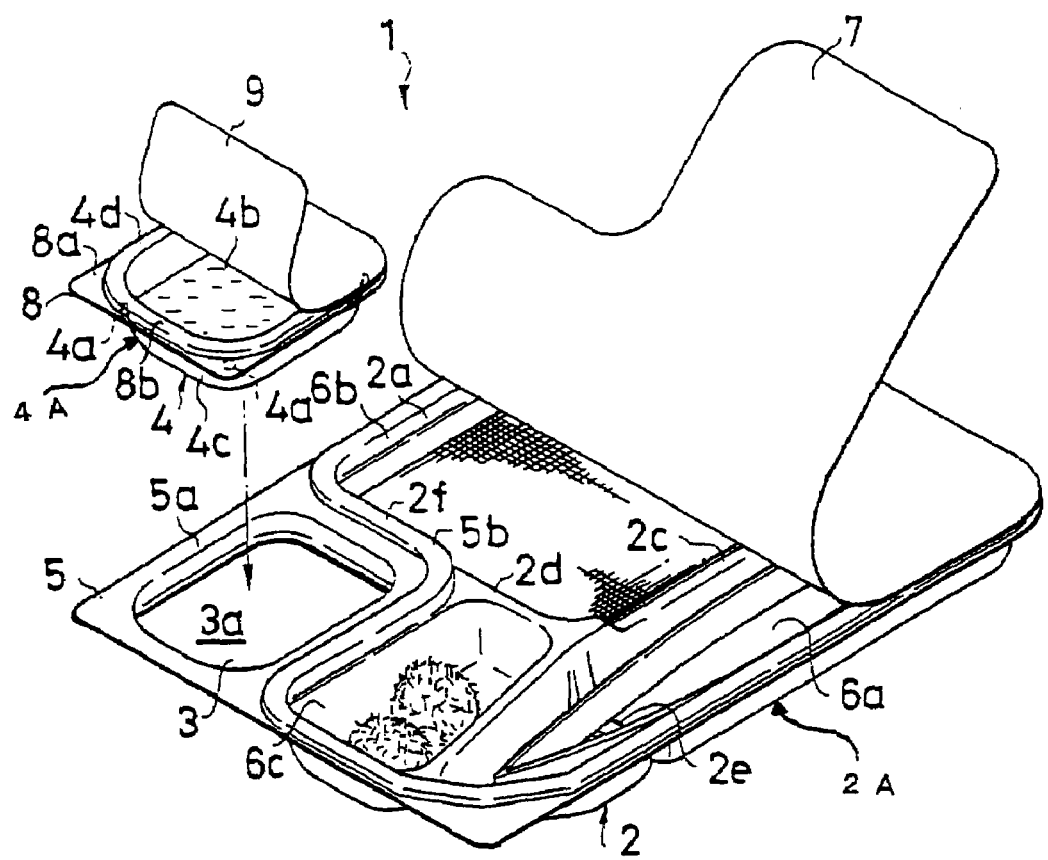
FIG. 1 (A) is a perspective view of one example of the medical kit of the present invention, and FIG. 1 (B) is a cross-sectional view in FIG. 1 (A).
Figure 1:
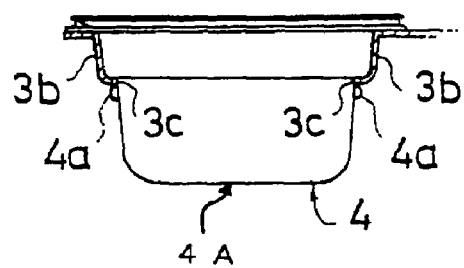
Figure 2:
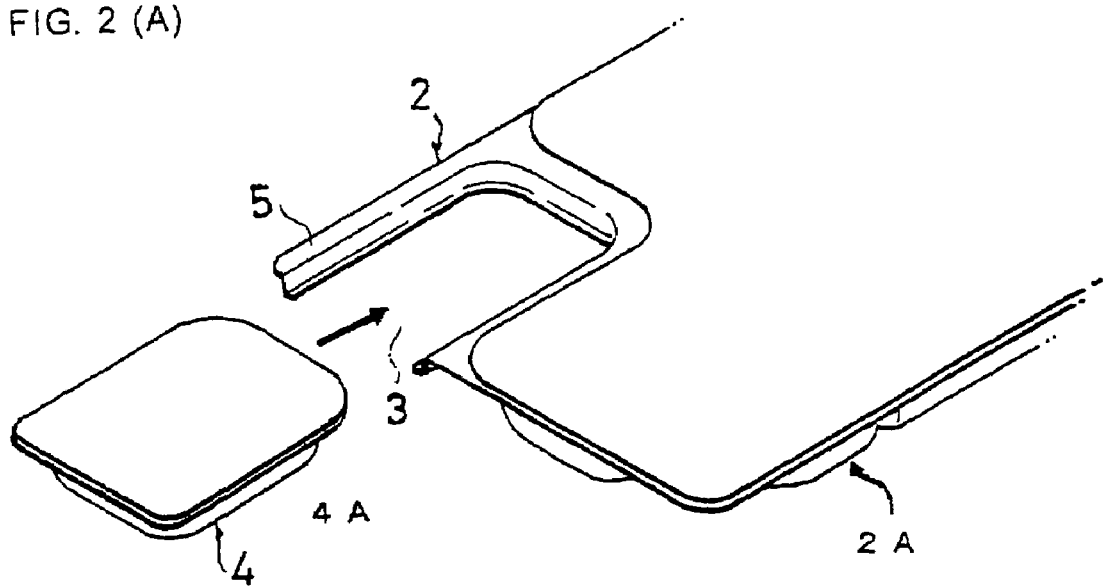
FIG. 2 (A) is an exploded perspective view showing another example of mounting portion 3, and FIG. 2 (B) is a cross-sectional view of the mounting portion 3 in FIG. 2 (A).
Figure 2:
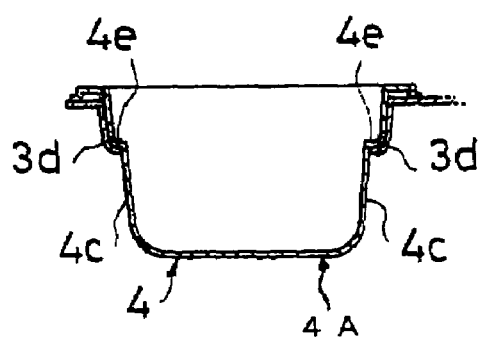

FIG. 1 (A) is an exploded perspective view of a medical kit 1, as one example of the present invention, FIG. 1 (B) is a sectional side view of a mounting portion 3 of the medical kit 1 shown in (A), FIG. 2 (A) is an exploded perspective view showing another example of mounting portion 3, and FIG. 2 (B) is a sectional side view of the mounting portion 3 in (A).

As shown in FIG. 1 (A), the medical kit 1 is provided with a medical instrument housing portion 2 housing a medical instrument and a medicinal solution housing portion 4 housing a medicinal solution, constituted so that the medicinal solution housing portion 4 may be integrated by detachably fitting it into a mounting portion 3 created in the medical instrument housing portion 2.

(Medical Instrument Housing Portion 2)

The medical instrument housing portion 2 can be formed by providing a tray-shaped medical instrument housing container 2A that houses medical instruments (including supplements for medical use) comprising any of a syringe, gauze, a bandage, blood coagulation tape, tweezers, a cotton ball, and the like, or a combination of two or more kinds among these, the medical instruments being housed inside the medical instrument housing container 2A and covered with a covering material 7.

The material quality of the medical instrument housing container 2A is not limited in particular; however, it is preferred that it is formed from a resin having a shape-retaining property. For instance, any resin among polystyrene, polyethylene, polypropylene, polyethylene terephthalate, amorphous polyethylene terephthalate, polybutylene terephthalate, or a polymer blend or a co-polymer of two or more kinds of these, or laminate resin with a laminated layer constitution, such as PP/EVOH/PP, and the like can be adopted. In addition, it is also preferred to select the material quality of the medical instrument housing container 2A by considering the sterilization method. The material quality is not chosen in particular in the case of gas sterilization, such as EOG; however, the use of a radiation-resistant material is preferred in case of radiation or electron beam sterilization, and the use of a heat-resistant material is preferred in case of autoclave sterilization.

A sheet body is formed from such resins, and this sheet body can be molded by a suitable molding means, such as vacuum forming, pressure forming, pressure-vacuum forming, to form the medical instrument housing container 2A. However, the source resin is not limited to the aforementioned resins.

The medical instrument housing container 2A is formed by having created a housing chamber 2a with a concavely depressed shape for housing a medical instrument, and a mounting portion 3 in which a medicinal solution housing portion 4 may be fitted. If the housing chamber 2a and the mounting portion 3 are provided, forming other structures is optional.

The housing chamber 2a housing the medical instrument is formed in such a way that, except for the part of forming the mounting portion 3, the sheet body is concavely depressed within the sheet plane of a sheet body, having a substantially rectangular shape when viewed from the top, to form a concave portion that may house a medical instrument, and at the same time, dividing walls 2c and 2d are created inside the concave portion by uplifting a bottom surface 2b, and compartment chambers 6a, 6b, and 6c are created inside the concave portion by the dividing walls 2c and 2d.

In so doing, the compartment chambers created inside the housing chamber 2a can be formed with a suitable number, shape, size, and the like. In case of the present example, three compartment chambers 6a, 6b, and 6c were created, the compartment chamber 6a being formed into a compartment where an elongated object, such as tweezers, is easily housed, the compartment chamber 6b being formed into a compartment where a flat-shaped object, such as gauze, is easily housed, and the compartment chamber 6c being formed into a compartment where a three-dimensional object, such as a cotton ball, is easily housed, respectively. Among them, the bottom surface of the compartment chamber 6a is formed as a laying portion 2e by slightly uplifting a portion of the bottom surface 2b and is formed in such a way that by laying the back end of tweezers and the like there, the tweezers and the like are easily taken out.

Note that the constitution of the interior of the housing chamber 2a can be any form. As one example, the bottom surface 2b can be formed to be an oblique surface, so that the medical instrument can easily be taken out.

In the present example, in terms of the shape seen from above, the housing chamber 2a is formed into a shape, wherein one corner within the sheet plane of a sheet body having a substantially rectangular shape is cut out into a rectangular shape; in other words, into a shape wherein a protruding portion having a substantially rectangular shape is created in a portion of a substantially rectangular shape; however, it can also be formed by using a sheet body having another rectangular shape, a substantially circular shape, a substantially elliptical shape, and other shape, instead of a sheet body having a substantially rectangular shape. Also, the shape of the housing chamber 2a is not limited to the shape described above and can be formed into any shape.

A flange portion 5 is left in the surroundings of where the housing chamber 2a is formed, within the sheet plane of the sheet body where the housing chamber 2a is formed, a seal portion 5b protruding with a suitable width and a suitable height being created around in this flange portion 5 so as to surround the entire perimeter of the housing chamber 2a, to attach a covering material 7 easily to this seal portion 5b.

The mounting portion 3 is a portion where a medicinal solution housing portion 4 is fitted; in other words, it is the top-fitting portion for the medicinal solution housing portion 4, formed within the sheet surface 5a, remaining on the sheet body where the housing chamber 2a is formed. That is to say, an opening 3a is created within the sheet surface 5a of the sheet body, where the bottom portion of the medicinal solution housing portion 4 can be inserted; at the same time, the inner peripheral portion of this opening 3a is curved towards the back side of the sheet to form an inner fitting edge portion 3b, so as to be lined with the lateral surface of the medicinal solution housing portion 4 when the bottom portion of the medicinal solution housing portion 4 is inserted into the opening 3a; furthermore, the end portion of this inner fitting edge portion 3b is folded inwards to form a fitting edge 3c.

The covering material 7 covers the housing chamber 2a, which houses a medical instrument and attaches to the seal portion 5b to seal the housing chamber 2a.

The material quality of the covering material 7 is not limited in particular; however, film or sheet materials consisting of, for instance, sterilization paper, polyethylene terephthalate, polyethylene, polypropylene, non-woven fabric, and the like, may be adopted, and selecting a material quality that is appropriate to the sterilization method is important. For instance, in case of sterilization by radiation such as gamma beam or electron beam sterilization, any material quality can be selected; among them, polyethylene terephthalate, polyethylene, polypropylene, and the like are preferred. In case of gas sterilization, such as EOG, sterilization paper, non-woven fabric, and the like are preferred; in addition, a composite material partly provided with a sterilization paper portion can also be used.

This covering material 7 is preferably attached to the seal portion 5b by adhesive means, such as a heat seal. However, any other means may be adopted.

(Medicinal Solution Housing Portion 4)

The medicinal solution housing portion 4 can be formed by providing with a medicinal solution housing container 4A, which is a separate body from the medical instrument housing container 2A, a medicinal solution being housed inside this medicinal solution housing container 4A and covering with a covering material 9.

The medicinal solution housing container 4A is formed into a cup-shaped container that may house a medicinal solution for disinfection, such as povidone iodine and alcohol, other fluid medicinal solution, therapeutic agent, distilled water, sterile water, or cotton balls or gauzes impregnated therewith. However, the shape of the medicinal solution housing container 4A is not limited to cup-shape and can be formed into any suitable shape.

The material quality of the medicinal solution housing container 4A is not limited in particular; however, adopting a sheet or a film consisting of a resin provided with shape-retaining property, chemical resistance, and barrier property to prevent permeation and volatilization of the medicinal solution and the like is preferred. For instance, polystyrene, polyethylene, polypropylene, polyethylene terephthalate, and the like can be preferably used.

The medicinal solution housing container 4A is formed by forming a housing chamber 4b concavely depressed into a substantially rectangular shape when viewed from above within the sheet plane of a sheet body having a substantially rectangular shape when viewed from above, and the sheet surface that does not form this housing chamber 4b is left as a flange portion 8.

Here, instead of a sheet body having a substantially rectangular shape when viewed from above, a sheet having another rectangular shape, a substantially circular shape, a substantially elliptical shape, and other shape can also be used, and the shape of the housing chamber 4a can also be formed into any shape.

In addition, the depth of the housing chamber 4b is preferably almost identical to the depth of the housing chamber 2a of the medical instrument housing portion 2.

The housing chamber 4b has a step portion created on a side surface 4c thereof, the lower side being slightly tapered through this step portion, and is formed in two steps so as to lower the capacity, a fitting protrusion 4a that protrudes outward being formed on a site that is close to the upper portion of the lower step portion on the side surface thereof (in the present example, at the site close to the upper portion of the angular corner portion on the side surface of the housing chamber 4b concavely depressed into a substantially rectangular shape), and is arranged in such a way that, when the bottom portion of the medicinal solution housing container 4A is inserted in the opening 3a of the mounting portion 3, the upper step portion on the side surface of the medicinal solution housing container 4A interlocks with the inner fitting edge portion 3b of the mounting portion 3, engaging the step portion of the side surface 4c of the housing chamber 4b and the fitting edge 3c to engage the medicinal solution housing container 4A so that it cannot pop out downward, and engaging the extremity of the fitting edge 3c and the fitting protrusion 4a to engage the medicinal solution housing container 4A so that it can also not pop out upwards, as shown in FIG. 1 (B).

In addition, a seal portion 8a protruding with a suitable width and a suitable height is formed in the flange portion 8 so as to surround the entire perimeter of the housing chamber 4b, making attachment of a covering material 9 to this seal portion 8a easy.

The covering material 9 covers the housing chamber 4b that houses the medicinal solution, is formed into a shape that follows the upper edge portion 4d of the housing chamber 4b (that is the seal portion 8a), and attaches it to the seal portion 8b with a method such as heat sealing, which is sufficient to seal the housing chamber 4b.

A different material quality than the covering material 7 is preferably used for covering material 9. Although the material quality thereof is not to be limited in particular, it is necessary that it be provided with water resistance and chemical resistance. One preferred example that can be cited is a composite sheet consisting of, for instance, thin metal film layers laminated on the surface of a sheet, which is a resin base material sheet. Specifically, a composite sheet consisting of thin metal film layers laminated by vapor depositing or laminating a metal, such as aluminum, on a resin base material sheet, such as polyethylene, polypropylene, and polyethylene terephthalate and the like, can be preferably used.

(Manufacturing of Medical Kit 1)

The following is adequate to manufacture a medical kit 1 using the above medical instrument housing container 2A and medicinal solution housing container 4A. However, it is not limited to the following method.

After housing medical instruments, such as, for instance, tweezers, gauze, and cotton ball (including those authorized as hygiene products, medical instruments, and miscellaneous articles for medical use), in the housing chamber 2a of the medical instrument housing container 2A, the housing chamber 2a is covered by attaching the covering material 7 and sealed by an adhesion method, such as heat sealing, then the medical instruments inside the housing chamber 2a are treated by sterilization.

In so doing, since deterioration of medicinal solution or explosion due to sterilization treatment and the like do not need to be considered, any sterilization treatment method can be adopted. For instance, radiation/electron beam sterilization wherein a radiation, such as gamma beam, is irradiated, gas sterilization, such as EOG sterilization, heat/pressure pasteurization by an autoclave, and the like, and any other sterilization treatment disclosed currently or in the future can be performed.

Note that the interior of the housing chamber 4b of the medicinal solution housing container 4A is filled with a medicinal solution (including antiseptic agent solution authorized by the Pharmaceutical Affairs Law), and the housing chamber 4b is covered by attaching the covering material 9 using an adhesion method, such as heat sealing, to seal the medicinal solution housing portion 4 separately from the above-mentioned medical instrument housing portion 2.

Note that, regarding filling with the medicinal solution, filling in an aseptic room is desirable from the purpose of use, such as in operative or postoperative disinfection of the affected area; however, from the utilization environment and the level of disinfection of hospitals, dialysis rooms, and the like currently in use, the medicinal solution housing container 4A and the covering material 9 may be disinfected beforehand and filling performed inside a clean room. Which filling method to adopt is ultimately determined by conforming to the product criteria relevant to the Pharmaceutical Affairs Law.

Then, the medical kit 1 can be completed by inserting the medicinal solution housing portion 4 into the opening 3a in the mounting portion 3 of the medical instrument housing container 2A, and fitting the fitting protrusion 4a of the medicinal solution housing container 4A with the fitting edge 3c in the mounting portion 3, to detachably assemble the medicinal solution housing portion 4.

In the above medical kit 1, the fitting edge 3c and the fitting protrusion 4a are formed in such a way that they fit; fitting means between the medical instrument housing container 2A and the medicinal solution housing container 4A is not limited to such fitting means, and any fitting structure can be adopted. However, fitting means where the medical instrument housing portion 2 and the medicinal solution housing portion 4 are detachable, that is to say, the medicinal solution housing portion 4 can be subsequently taken out, is preferred. If the medicinal solution housing portion 4 can be subsequently taken out in this way, when using the medical kit 1, the medicinal solution housing portion 4 can be taken out from the medical instrument housing portion 2 as necessary and used, which is very convenient.

Presenting here an example of fitting means that is different from the above description, as shown in FIG. 2, the mounting portion 3 can be made to be of a constitution where it has an interlocking edge 3d obtained by cutting out the edge at one end of the flange portion 5 of the medical instrument housing container 2A into a substantially rectangular shape, sending downward the edges on both sides thereof in parallel, and bending the lower extremity so that they face each other, and the medicinal solution housing container 4A can be made to be of a constitution wherein the top of the side surface 4c has been extended outward to form an interlocking portion 4e that can interlock with the interlocking edge 3d. In this way, the medicinal solution housing container 4A can slide from the side and fitted.

In addition, in the present example, the mounting portion 3 is created at one corner of the medical instrument housing container 2A; however, it is not limited to this and can be created at a suitable location.

Furthermore, the constitution may be a plurality of medicinal solution housing portions 4 mounted with respect to one medical instrument housing portion 2, in which case it suffices to form a plurality of mounting portions 3 accordingly.

The following describes another constitution example (reference example) different from the above for comparison with the present invention.

Figure 3:
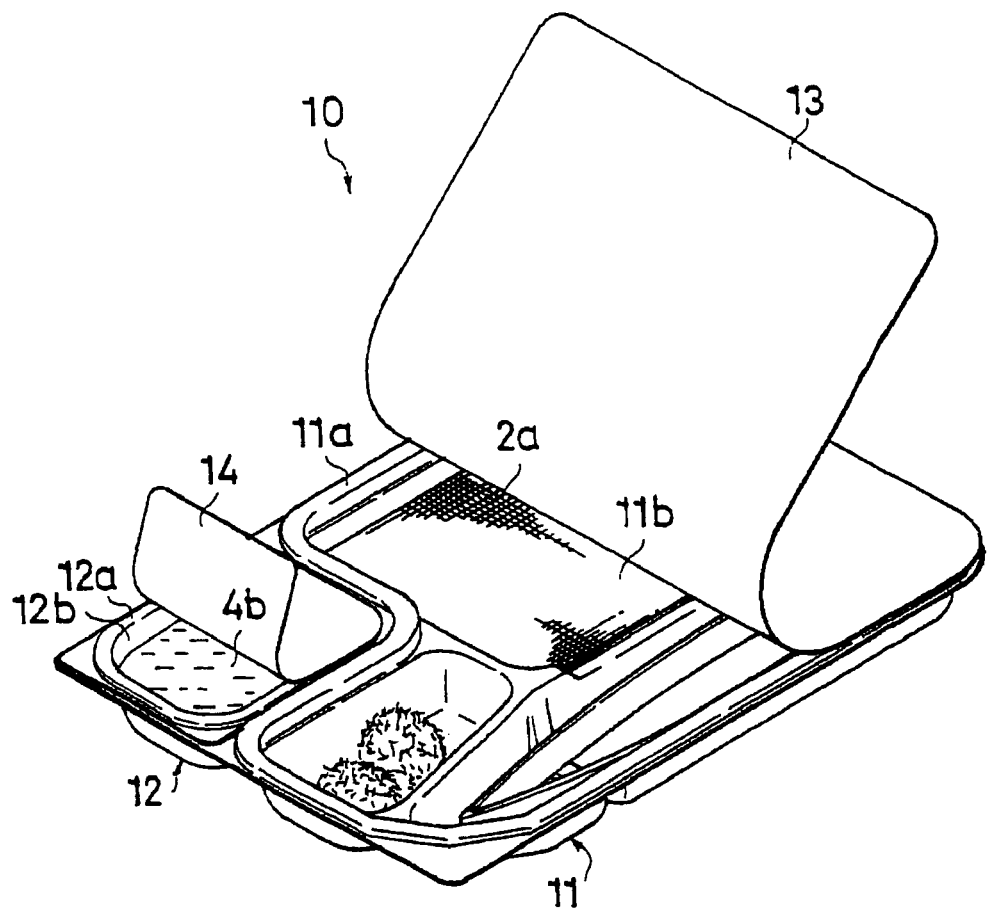
FIG. 3 is a perspective view showing a medical kit as a reference example.
Figure 4:
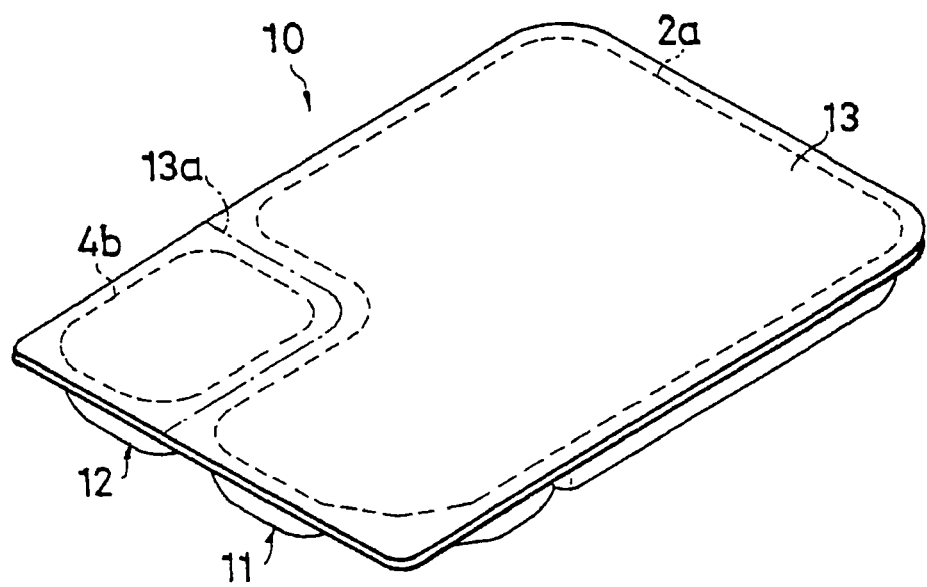
FIG. 4 is a perspective view showing an example of variation of the covering material in FIG. 3.

FIG. 3 is a perspective view showing a medical kit 10 as a reference example, and FIG. 4 is a perspective view showing an example of variation of the covering material in FIG. 3.

The medical kit 10 is of a constitution in which the interior of a medicinal solution housing portion 12 is filled with a medicinal solution and sealed with a covering material 14; this is detachably fitted into a medical instrument housing portion 11, whereafter the medical instrument housing portion 11 and the medicinal solution housing portion 12 are covered with another covering material 13.

As shown in FIG. 3, in this medical kit 10, the upper edge portion 11a of the medical instrument housing portion 11 and the upper edge portion 12a of the medicinal solution housing portion 12 are formed in such a way that they are at the same elevation, that is to say, in one plane, when the medicinal solution housing portion 12 is fitted into the medical instrument housing portion 11.

The covering material 13 is provided with a size that can cover together the opening 11b of the medical instrument housing portion 11 and the opening 12b of the medicinal solution housing portion 12.

The material quality of the covering material 14 is different from the above-mentioned covering material 13, and the material thereof is not limited in particular. However, the use of a material having water resistance and chemical resistance is preferred. For instance, a composite sheet consisting of, for instance, thin metal film layers laminated on the surface of a sheet, which is a resin base material sheet, can be preferably used, and specifically, a composite sheet consisting of thin metal film layers laminated by vapor depositing or laminating a metal, such as aluminum, on a resin base material sheet, such as polyethylene, polypropylene, and polyethylene terephthalate, can be preferably used.

Note that, depending on the sterilization method, there may be cases where a sheet with a material quality that reflects radiation or electron beam is preferred.

The medical kit 10 consisting of the above constitution can be manufactured (assembled) as follows. However, the medical instrument housing portion 11 and the medicinal solution housing portion 12 consist of the same constitution as the medical instrument housing portion 2 and the medicinal solution housing portion 3 described above, except for the constitution described below.

The interior of the housing chamber of the medicinal solution housing portion 12 is filled with a medicinal solution and sealed with the covering material 14 by an adhesion method, such as heat sealing.

Next, medical instruments, such as, for instance, tweezers, gauze, and a cotton ball, are housed inside the housing chamber of the medical instrument housing portion 11, and the above medicinal solution housing portion 12 is detachably assembled to the medical instrument housing portion 11. Then, the medical instrument housing portion 11 and the medicinal solution housing portion 12 are sealed by covering with and attaching the covering material 13 by an adhesion method, such as heat sealing, followed by performing a sterilization treatment to complete the medical kit 10.

In so doing, a sterilization treatment method that does not have the potential to give rise to deterioration of the medicinal solution housed in the medicinal solution housing portion 12 or explosion by evaporation of the medicinal solution inside due to the sterilization treatment and the like must be adopted as the method for sterilization treatment. Methods that can be adopted among the currently known sterilization treatment methods include only methods in which radiation, such as gamma beam, is irradiated; however, adoption of a new sterilization treatment developed in the future is possible.

As shown in FIG. 4, a cutting line 13a, such as a perforated line, may be created in the covering material 13 where the housing chamber 2a of the medical instrument housing portion 11 and the housing chamber 4b of the medicinal solution housing portion 12 are separated. This allows for a medical kit 10 wherein, when unsealing, it is possible to unseal only the medical instrument housing portion 11 or the medicinal solution housing portion 12 by cutting at the cutting line 13a while unsealing.

(Comparison Between Medical Kit 1 and Medical Kit 10)

When the medical kit 1 as one example of the present invention and the medical kit 10 as a reference example are compared, the medical kit 1 is better from the points of safety, manufacturing cost, user-friendliness, functionality, and the like.

That is to say, in the case of medical kit 10, since the medicinal solution housing portion 12 also receives sterilization treatment simultaneously when sterilizing the medical instrument housing portion 11, there is the possibility by the sterilization treatment of deterioration of the medicinal solution or explosion of the medicinal solution housing portion 12 due to evaporation of the medicinal solution and the like. For this reason, the method for the sterilization treatment, the material quality of the covering material 14, and the like are limited to those that do not give rise to these problems. In contrast to this, in the case of medical kit 1, since it is possible to treat by sterilization only the medicinal solution housing portion 2, there is no need to consider the influence of the sterilization treatment on the medicinal solution housing portion 4 or the housed medicinal solution, and the method of sterilization treatment and the covering material 9 can be selected freely. Therefore, a better product on the points of safety, manufacturing cost, user-friendliness, functionality, and the like can be provided.

What is claimed is:

1. A medical kit comprising:
   a medicinal solution housing container having a medicinal solution housing chamber for housing a medicinal solution, and said medicinal solution housing chamber being closed by a first covering material, and
   a medical instrument housing portion, separate from said medicinal solution housing container, comprising a medical instrument housing chamber for housing a medical instrument, said medical instrument housing chamber being closed by a second covering material different from said first covering material,
   wherein the medicinal solution housing and the medical instrument housing comprise shape retaining base portions,
   the medical instrument housing comprises a first shape having a cut-out portion, the medicinal solution housing portion comprises a second shape corresponding to the cut-out portion,
   the first covering material does not overlap the second covering material, and
   the medicinal solution housing container is removeably attached to the medical instrument housing portion at the cut-out portion, such that the medicinal solution housing container can be detached from the medicinal instrument housing portion without removing the second covering material from the medical instrument housing container, and such that the shape retaining base portion of the medicinal solution housing attaches to the shape retaining base portion of the medical instrument housing at the cut-out portion by a means for removeably attaching said base portions.

2. The medical kit as recited in claim 1 wherein the medical instrument housing container comprises a flange portion for mounting said medical solution housing container to said medical instrument housing container.

3. The medical kit as recited in claim 1 wherein the medicinal solution housing chamber holds a medicinal solution and the medical instrument housing chamber holds at least one sterilized medical instrument.

4. The medical kit as recited in claim 2 wherein the medicinal solution housing chamber holds a medicinal solution and the medical instrument housing chamber holds at least one medical instrument.

5. The medical kit as recited in claim 1 wherein said cut-out portion has no closed bottom.

6. The medical kit as recited in claim 1 wherein said cut-out portion does not define a compartment.

7. A medical kit comprising:
a sheet body formed from a shape retaining resin and defining a sheet plane, the sheet body being concavely depressed within the sheet plane of the sheet body to form a medical instrument housing portion having at least one chamber for housing a medical instrument and being cut out to form at least one cut-out portion, said medical instrument housing portion having a first seal portion protruding above said sheet plane and said at least one cut-out portion being an opening in the sheet body that does not define a chamber and being shaped to form a mounting portion having a first edge interlocking portion;

a medicinal solution housing formed from a shape retaining resin, being a body separate from said sheet body and having a medicinal solution housing chamber for housing a medicinal solution, said medicinal solution housing being sized to be received in said cut-out portion and having a second sealing portion around a periphery of said medical solution housing chamber and a second edge interlocking portion for engaging said first edge interlocking portion of said sheet body, and a first covering for sealably engaging said first seal portion and for closing the at least one chamber of said medical instrument housing portion and a second covering for sealably engaging said second seal portion and for closing said medicinal solution housing chamber, said first covering material being different from said second covering material, and said first and second covering materials do not overlap when covering respective housings;

wherein the medicinal solution housing is removeably attached to the medical instrument housing portion, such that the medicinal solution housing can be detached from the medical instrument housing portion without removing the first covering material from the medical instrument housing portion.

8. The medical kit as recited in claim 7 wherein the inner peripheral portion of the cut out portion is curved towards a back side of the sheet to form an inner fitting edge portion so as to be aligned with a lateral surface of the medicinal solution housing when a bottom portion of the medicinal solution housing is inserted into the cut out portion.

9. The medical kit as recited in claim 8 wherein the end portion of the inner fitting edge portion is folded inwards to form said fitting edge.

10. The medical kit as recited in claim 8,
wherein the sheet at the cut out is depressed to a depth below the sheet plane and forms a fitting edge, and
wherein the medicinal solution housing has a protrusion disposed on a side surface to substantially said depth, whereby upon assembly, the protrusion and fitting edge engage to secure said medicinal solution housing in said sheet body.

11. The medical kit as recited in claim 7,
wherein the cut-out is defined by a closed periphery and the housing chamber is detachable by movement vertically.

12. The medical kit as recited in claim 7,
wherein the cutout is defined by an open periphery and the housing chamber is detachable by movement horizontally.

* * * * *